(12) United States Patent
Scott et al.

(10) Patent No.: US 9,826,963 B2
(45) Date of Patent: Nov. 28, 2017

(54) MINIMALLY INVASIVE IMPLANTABLE NEUROSTIMULATION SYSTEM

(71) Applicant: Medtronic, Inc., Minneapolis, MN (US)

(72) Inventors: Erik R. Scott, Maple Grove, MN (US); John E. Kast, Hugo, MN (US); Xuan K. Wei, Minnetonka, MN (US); Todd V. Smith, Shoreview, MN (US); Joel A. Anderson, Brooklyn Park, MN (US); Forrest C. M. Pape, New Brighton, MN (US); Duane L. Bourget, Albertville, MN (US); Timothy J. Denison, Minneapolis, MN (US); David A. Dinsmoor, St. Paul, MN (US); Randy S. Roles, Elk River, MN (US); Stephen J. Roddy, Maple Grove, MN (US)

(73) Assignee: Medtronic, Inc., Minneapolis, MN (US)

( * ) Notice: Subject to any disclaimer, the term of this patent is extended or adjusted under 35 U.S.C. 154(b) by 585 days.

(21) Appl. No.: 14/098,672

(22) Filed: Dec. 6, 2013

(65) Prior Publication Data
US 2014/0163644 A1 Jun. 12, 2014

Related U.S. Application Data

(60) Provisional application No. 61/734,425, filed on Dec. 7, 2012, provisional application No. 61/777,804, filed
(Continued)

(51) Int. Cl.
*A61N 1/372* (2006.01)
*A61N 1/36* (2006.01)
(Continued)

(52) U.S. Cl.
CPC .......... *A61B 17/00234* (2013.01); *A61N 1/02* (2013.01); *A61N 1/05* (2013.01);
(Continued)

(58) Field of Classification Search
CPC .. A61N 1/36139; A61N 1/05; A61N 1/37247; A61N 1/37252; A61N 1/36057;
(Continued)

(56) References Cited

U.S. PATENT DOCUMENTS

| 3,971,388 A | 7/1976 | Cowdery |
| 6,051,017 A | 4/2000 | Loeb et al. |

(Continued)

FOREIGN PATENT DOCUMENTS

| CN | 101522256 A | 9/2009 |
| CN | 101522260 A | 9/2009 |

(Continued)

OTHER PUBLICATIONS

International Preliminary Report on Patentability from International Application No. PCT/US2013/073487, dated Jun. 18, 2015, 9 pp.
(Continued)

*Primary Examiner* — Mark W Bockelman
(74) *Attorney, Agent, or Firm* — Shumaker & Sieffert, P.A.

(57) ABSTRACT

An external medical device generates a drive signal inductively coupled to an implantable coil from an external coil. A regulator module coupled to the implantable coil generates an output signal in response to the inductively coupled signal and a feedback signal correlated to an amplitude of the inductively coupled signal. A signal generator receives the output signal for generating a therapeutic electrical stimulation signal. The control module adjusts the drive signal in response to the feedback signal to control the electrical stimulation signal.

27 Claims, 9 Drawing Sheets

Related U.S. Application Data on Mar. 12, 2013, provisional application No. 61/734,429, filed on Dec. 7, 2012, provisional application No. 61/777,949, filed on Mar. 12, 2013, provisional application No. 61/734,446, filed on Dec. 7, 2012, provisional application No. 61/777,824, filed on Mar. 12, 2013, provisional application No. 61/777,838, filed on Mar. 12, 2013, provisional application No. 61/734,436, filed on Dec. 7, 2012, provisional application No. 61/777,787, filed on Mar. 12, 2013.

(51) Int. Cl.

| | | |
|---|---|---|
| *A61B 17/00* | (2006.01) | |
| *A61N 1/05* | (2006.01) | |
| *A61N 1/378* | (2006.01) | |
| *A61N 1/02* | (2006.01) | |
| *A61N 1/375* | (2006.01) | |

(52) U.S. Cl.
CPC ............ *A61N 1/0551* (2013.01); *A61N 1/36* (2013.01); *A61N 1/3605* (2013.01); *A61N 1/36007* (2013.01); *A61N 1/36057* (2013.01); *A61N 1/36067* (2013.01); *A61N 1/36071* (2013.01); *A61N 1/36139* (2013.01); *A61N 1/3727* (2013.01); *A61N 1/3754* (2013.01); *A61N 1/3756* (2013.01); *A61N 1/3787* (2013.01); *A61N 1/37205* (2013.01); *A61N 1/37223* (2013.01); *A61N 1/37235* (2013.01); *A61N 1/37247* (2013.01); *A61N 1/37252* (2013.01); *A61N 1/36021* (2013.01); *A61N 1/36053* (2013.01); *A61N 1/375* (2013.01); *A61N 1/37211* (2013.01); *F04C 2270/0421* (2013.01)

(58) Field of Classification Search
CPC .. A61N 1/3787; A61N 1/3727; A61N 1/3754; A61N 1/02; A61N 1/0551; A61N 1/36; A61N 1/3605; A61N 1/37235; A61N 1/37205; A61N 1/375; A61N 1/3756; A61N 1/36007; A61N 1/36021; A61N 1/36053; A61N 1/36067; A61N 1/36071; A61N 1/37211; A61N 1/37223; A61B 17/00234

See application file for complete search history.

(56) References Cited

U.S. PATENT DOCUMENTS

| | | |
|---|---|---|
| 6,975,906 B2 | 12/2005 | Rusin et al. |
| 7,054,692 B1 | 5/2006 | Whitehurst et al. |
| 7,103,415 B2 | 9/2006 | Probst et al. |
| 7,444,184 B2 * | 10/2008 | Boveja ............... A61N 1/36014 607/118 |
| 7,460,913 B2 | 12/2008 | Kuzma et al. |
| 7,467,014 B2 | 12/2008 | Fuller et al. |
| 7,496,404 B2 * | 2/2009 | Meadows ........... A61N 1/0553 607/43 |
| 7,860,570 B2 | 12/2010 | Whitehurst et al. |
| 7,949,395 B2 | 5/2011 | Kuzma |
| 8,989,861 B2 * | 3/2015 | Su et al. .................. 607/41 |
| 2003/0114905 A1 | 6/2003 | Kuzma |
| 2005/0021119 A1 | 1/2005 | Sage et al. |
| 2005/0092507 A1 | 5/2005 | Marshall et al. |
| 2006/0085041 A1 | 4/2006 | Hastings et al. |
| 2007/0100383 A1 | 5/2007 | Pastore et al. |
| 2007/0123923 A1 | 5/2007 | Lindstrom et al. |
| 2007/0156204 A1 | 7/2007 | Denker et al. |
| 2008/0058871 A1 | 3/2008 | Libbus et al. |
| 2008/0086181 A1 | 4/2008 | Amurthur et al. |
| 2009/0118778 A1 | 5/2009 | Biggs, Jr. et al. |
| 2009/0149900 A1 | 6/2009 | Moffitt et al. |
| 2009/0157147 A1 | 6/2009 | Cauller et al. |
| 2010/0023102 A1 | 1/2010 | Spruit |
| 2010/0106223 A1 | 4/2010 | Grevious et al. |
| 2010/0152808 A1 | 6/2010 | Boggs, II |
| 2011/0301670 A1 | 12/2011 | Gross et al. |
| 2012/0130398 A1 | 5/2012 | Ackermann et al. |
| 2012/0303105 A1 | 11/2012 | Askarinya et al. |

FOREIGN PATENT DOCUMENTS

| | | |
|---|---|---|
| CN | 101528303 A | 9/2009 |
| WO | 2004002572 A1 | 1/2004 |
| WO | 2009134466 A1 | 11/2009 |
| WO | 2010059096 A1 | 5/2010 |

OTHER PUBLICATIONS

U.S. Appl. No. 14/098,608, filed Dec. 6, 2013, by Tischendorf et al.
U.S. Appl. No. 14/098,621, filed Dec. 6, 2013, by Tischendorf et al.
U.S. Appl. No. 14/099,462, filed Dec. 6, 2013, by Tischendorf et al.
U.S. Appl. No. 14/098,728, filed Dec. 6, 2013, by Dinsmoor et al.
International Search Report and Written Opinion from counterpart International Application No. PCT/US2013/073487, dated Feb. 5, 2014, 14 pages.

\* cited by examiner

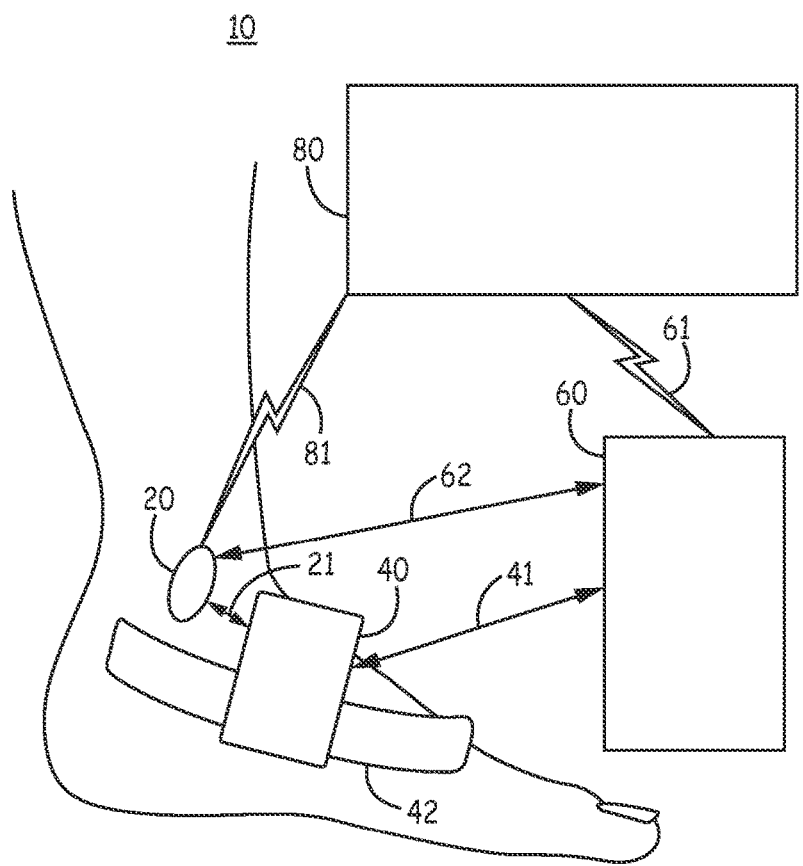
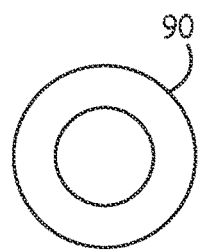
FIG. 1

MINIMALLY INVASIVE IMPLANTABLE NEUROSTIMULATION SYSTEM

CROSS-REFERENCE TO RELATED APPLICATIONS

The present application claims priority to U.S. Provisional Patent Application No. 61/734,425, filed Dec. 7, 2012, which application is incorporated herein by reference as if re-written in its entirety.

The present application claims priority to U.S. Provisional Patent Application No. 61/777,804, filed Mar. 12, 2013, which application is incorporated herein by reference as if re-written in its entirety.

The present application claims priority to U.S. Provisional Patent Application No. 61/734,429, filed Dec. 7, 2012, which application is incorporated herein by reference as if re-written in its entirety.

The present application claims priority to U.S. Provisional Patent Application No. 61/777,949, filed Mar. 12, 2013, which application is incorporated herein by reference as if re-written in its entirety.

The present application claims priority to U.S. Provisional Patent Application No. 61/734,446, filed Dec. 7, 2012, which application is incorporated herein by reference as if re-written in its entirety.

The present application claims priority to U.S. Provisional Patent Application No. 61/777,824, filed Mar. 12, 2013, which application is incorporated herein by reference as if re-written in its entirety.

The present application claims priority to U.S. Provisional Patent Application No. 61/777,838, filed March 12, 2013, which application is incorporated herein by reference as if re-written in its entirety.

The present application claims priority to U.S. Provisional Patent Application No. 61/734,436, filed Dec. 7, 2012, which application is incorporated herein by reference as if re-written in its entirety.

The present application claims priority to U.S. Provisional Patent Application No. 61/777,787, filed Mar. 12, 2013, which application is incorporated herein by reference as if re-written in its entirety.

FIELD OF THE DISCLOSURE

The disclosure relates generally to implantable neurostimulation systems and in particular to minimally invasive neurostimulation systems.

SUMMARY

Various exemplary embodiments of a minimally invasive implantable medical device (IMD) system are described. In some embodiments, the IMD system can include an external power supply that is inductively coupled to an IMD. Various exemplary external coil arrangements are described for coupling with an implanted coil for power transmission. A power feedback control signal transmitted from the IMD, which may be embodied as a neurostimulator in some examples, to the external device may be used to control a drive signal applied to an external coil and inductively coupled to an implanted coil. A regulator module of the IMD generates an output signal in response to the inductively coupled signal and provides the output signal to a signal generator for powering generation of a therapeutic electrical signal delivered to a target therapy site. The feedback signal is correlated to the inductively coupled signal and may be generated in response to a measurement of the output signal, the therapeutic electrical signal, or a physiological response to the therapeutic electrical signal in some examples. Adjustments to the therapeutic electrical signal are made by adjusting the drive signal in some embodiments. An activity sensor may be included and, responsive to detection of an activity state, the therapeutic electrical signal may be withheld by inhibiting the drive signal. Other exemplary aspects of the IMD system relating to inductively coupled power, patient management and therapy control are described.

BRIEF DESCRIPTION OF THE DRAWINGS

FIG. 1 is a schematic diagram of an exemplary minimally invasive IMD system capable of delivering a neurostimulation therapy.

DETAILED DESCRIPTION

Figure 2:
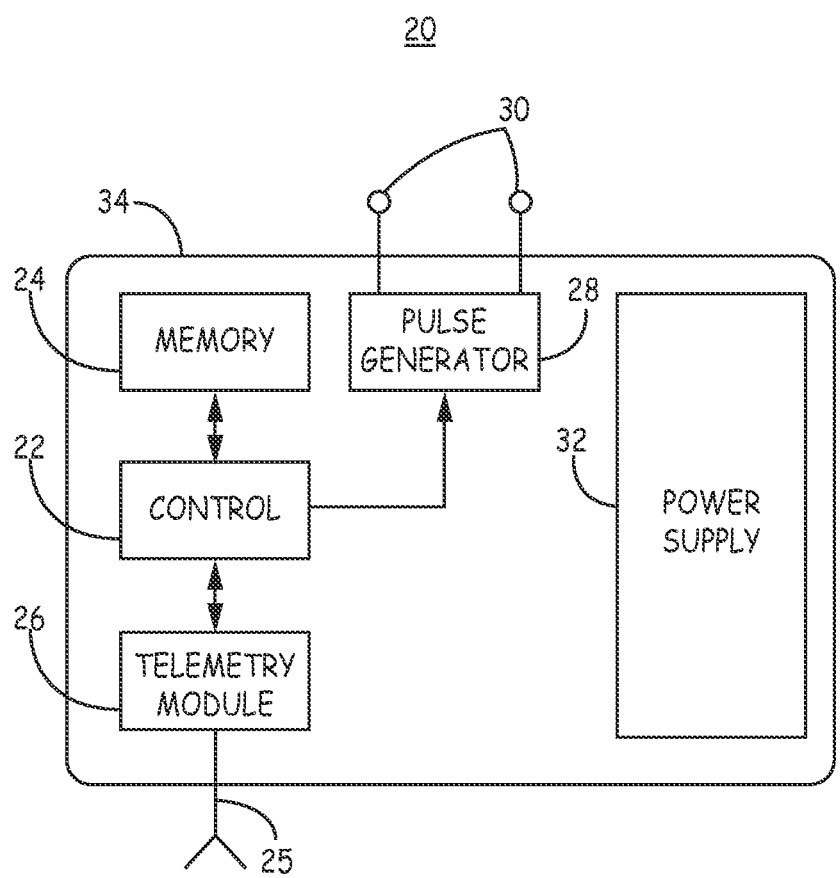
FIG. 2 is a functional block diagram of the IMD shown in FIG. 1 according to one embodiment.

Applicants have an appreciation that implantable medical device (IMD) technology is continually advancing as new applications are developed for automated therapy delivery in patients. Such advances may be further enhanced by using devices of reduced size and weight, which makes implantation of such devices less invasive and chronic use more comfortable for the patient. Additionally, applicants recognize that such enhancements such as improved power supply systems, wireless telemetry systems for communication with the implanted device, tools for performing implantation procedures, apparatus and methods for targeting a delivered therapy at desired location, and other system improvements can also enhance therapies in a manner that saves cost, conserves energy and minimizes any burden placed on the patient or clinician. Accordingly, Applicants recognize a need for improved, minimally-invasive implantable medical device systems and associated methods of use for providing patient monitoring and/or therapy delivery. Certain exemplary embodiments disclosed herein may obtain some or all of the aforementioned advantages and enhancements.

In the following description, references are made to illustrative embodiments. Various embodiments of an implantable neurostimulation (INS) system for delivering an electrical stimulation therapy to a targeted neural site are described. However, it is recognized that the various embodiments described herein may be implemented in numerous types of implantable medical device (IMD) systems, including, for example, implantable sensors or monitoring devices, implantable communication devices, and other types of implantable therapy delivery systems. The various embodiments of systems described herein and associated methods of use promote and facilitate minimally invasive INS systems in which the incision size and time required to implant and anchor the device can be minimized. The INS systems are designed to minimize cost, size and invasiveness of the device while providing efficacious therapy delivery (and/or accurate monitoring in a sensing-only device).

FIG. 1 is a schematic diagram of a minimally invasive INS system 10 capable of delivering a neurostimulation therapy. System 10 includes an IMD 20, an external device 40 enabled for transmitting signals to IMD 20, a patient programming device 60 enabled for bidirectional communication with IMD 20 and/or external device 40, and a physician programming device 80 according to one illustrative embodiment. In the illustrative embodiments described herein, communication between components included in the INS system 10 is configured to be bidirectional communication, however it is recognized that in some embodiments communication between two or more system components may be unidirectional.

IMD 20 includes circuitry for delivering neurostimulation pulses enclosed in a sealed housing and coupled to therapy delivery electrodes. In various embodiments, IMD 20 may include one or more of a primary battery cell, a rechargeable battery cell, and an inductively coupled power source for providing power for generating and delivering stimulation pulses and powering other device functions such as communication functions.

In some embodiments, IMD 20 is less than approximately 15 mm in length and less than approximately 1 cc in volume. In illustrative embodiments, the term "approximately" as used herein may indicate a value of ±10% of a stated value or may correspond to a range of manufacturing specification tolerances. In other examples, IMD 20 may be less than approximately 10 mm in length and may be less than approximately 0.6 cc in volume. IMD 20 may be approximately 0.1 cc in volume in some embodiments. The embodiments described herein are not limited to a particular size and volume of IMD 20, but are generally implemented to enable the use of a reduced size device for minimally invasive implantation procedures and minimized discomfort to a patient. It is recognized, however, that the various INS systems described herein may be implemented in conjunction with a wide variety of IMD sizes and volumes adapted for a particular therapy or monitoring application.

External device 40 may be a wearable device including a strap 42 or other attachment member(s) for securing external device 40 to the patient in operable proximity to IMD 20. When IMD 20 is provided with rechargeable battery cell(s), external device 40 may be embodied as a recharging unit for transmitting power, for example inductive power transmission from external device 40 to IMD 20. In this embodiment, programming device 60 may be a patient handheld device that is used to initiate and terminate therapy delivered by IMD 20 via a bidirectional wireless telemetry link 62. Alternatively, programming device 60 could be operated by a patient for communicating with wearable external device 40 to control therapy on and off times and other therapy control parameters, which are transmitted to IMD 20 via communication link 21. Programming device 60 may communicate with wearable external device 40 via a bidirectional wireless telemetry link 41 that may establish communication over a distance of up to a few feet or more, enabling distance telemetry such that the patient need not position programming device 60 directly over IMD 20 to control therapy on and off times or perform other interrogation or programming operations (e.g., programming of other therapy control parameters).

When IMD 20 includes primary cell(s), a wearable external device 40 may be optional. Programming of IMD 20 may be performed by the programming device 60, using near- or distance-telemetry technology for establishing bidirectional communication link 62 for transmitting data between programmer 60 and IMD 20. Programming device 60 may be used by a patient or clinician to set a therapy protocol that is performed automatically by IMD 20. Programming device 60 may be used to manually start and stop therapy, adjust therapy delivery parameters, and collect data from IMD 20, e.g. data relating to total accumulated therapy delivery time or other data relating to device operation or measurements taken by IMD 20.

When IMD 20 is configured as an externally powered device, external device 40 may be a power transmission device that is worn by the patient during a therapy session to provide power needed to generate stimulation pulses. For example, external device 40 may be a battery powered device including a primary coil used to inductively transmit power to a secondary coil included in IMD 20. External device 40 may include one or more primary and/or rechargeable cells and therefore may include a power adaptor and plug for re-charging in a standard 110V or 220V wall outlet, for example.

It is contemplated that in some embodiments the functionality required for transmitting power to IMD 20 when IMD 20 is embodied as a rechargeable or externally powered device and for programming the IMD 20 for controlling therapy delivery may be implemented in a single external device. For example, power transmission capability of external device 40 and programming capabilities of patient programmer 60 may be combined in a single external device, which may be a wearable or handheld device.

Physician programming device 80 may include increased programming and diagnostic functionality compared to patient programming device 60. For example, physician programming device 80 may be configured for programming all neurostimulation therapy control parameters, such as but not limited to pulse amplitude, pulse width, pulse shape, pulse frequency, duty cycle, therapy on and off times, electrode selection, and electrode polarity assignments.

Patient programming device 60 may be limited to turning therapy on and/or off, adjusting a start time of therapy, and/or adjusting a pulse amplitude without giving access to the patient to full programming functions such that some programming functions and programmable therapy control parameters cannot be accessed or altered by a patient.

Physician programming device 80 may be configured to communicate directly with IMD 20 via wireless, bidirectional telemetry link 81, for example during an office visit. Additionally or alternatively, physician programming device 80 may be operable as remote programming instrument used to transmit programming commands to patient programming device 60 via a wired or wireless communication network link 61, after which patient programming device 60 automatically transmits programming data to IMD 20 via bidirectional telemetry link 62 (or via wearable external device 40 and link 21).

In some embodiments, the patient may be provided with a magnet 90 for adjusting operation of IMD 20. For example, application of magnet 90 may turn therapy on or off or cause other binary or stepwise adjustments to IMD 20 operations.

While IMD 20 is shown implanted along a portion of the lower leg of a patient, IMD 20 could be implanted at numerous sites according to patient need and the particular medical application. In the illustrative embodiment, IMD 20 is provided for stimulating the tibial nerve of the patient to treat overactive bladder syndrome and is merely one example of the type of medical application for which INS system 10 may be used. IMD 20 may be positioned along a medial portion of the lower leg, e.g. posterior to the medial malleolus and superior to the flexor retinaculum. In another example, IMD 20 may be implanted to deliver a stimulation therapy to muscles of the pelvic floor, such as periurethral muscles or the external urethral sphincter for treating symptoms of urinary incontinence or overactive bladder syndrome. In such examples, the IMD 20 may be delivered intravaginally. In other examples, IMD 20 may be deployed for delivering neurostimulation therapy to an acupuncture point for treatment of a symptom associated with the acupuncture point. IMD 20 may be implemented in an INS system for providing numerous types of neurostimulation therapies, such as for pain control, autonomic nervous system modulation, functional electrical stimulation, tremor, and more.

FIG. 2 is a functional block diagram of IMD 20 according to one embodiment. IMD 20 includes a housing 34 enclosing a control unit 22 and associated memory 24, a telemetry module 26, and a pulse generator 28 coupled to electrodes 30. IMD 20 includes a power supply 32, which as described above may include any of a primary battery cell, a rechargeable battery cell, or a secondary coil of an externally powered system.

Control unit 22 may include any one or more of a microprocessor, a controller, a digital signal processor (DSP), an application specific integrated circuit (ASIC), a field-programmable gate array (FPGA), or equivalent discrete or integrated logic circuitry. In some examples, control unit 22 may include multiple components, such as any combination of one or more microprocessors, one or more controllers, one or more DSPs, one or more ASICs, or one or more FPGAs, as well as other discrete or integrated logic circuitry. The functions attributed to control unit 22 herein may be embodied as software, firmware, hardware or any combination thereof. In one example, a neurostimulation therapy protocol may be stored or encoded as instructions in memory 24 that are executed by controller 22 to cause pulse generator 28 to deliver the therapy via electrodes 30 according to the programmed protocol.

Memory 24 may include computer-readable instructions that, when executed by controller 22, cause IMD 20 to perform various functions attributed throughout this disclosure to IMD 20. The computer-readable instructions may be encoded within memory 24. Memory 24 may comprise non-transitory computer-readable storage media including any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital media, with the sole exception being a transitory propagating signal.

Telemetry module 26 and associated antenna 25 are provided for establishing bidirectional communication with wearable external device 40, patient programmer 60 and/or physician programmer 80. Examples of communication techniques used by IMD 20 and a programming device 60 or 80 include low frequency or radiofrequency (RF) telemetry, which may be an RF link established via Bluetooth, WiFi, or MICS, for example. Antenna 25 may be located within, along or extend externally from housing 34.

In one embodiment, telemetry module 26 is implemented as a Near Field Communication (NFC) target device capable of receiving NFC signals and harvesting power from the carrier signal. One example of a commercially available NFC target device is the M24LR16E-R dual interface EEPROM, available from STMicroelectronics, Huntsville, Ala., USA.

NFC is one commercially available, industry standardized short-range inductive communication technology that could be implemented in telemetry module 26 and an external device communicating with IMD 20, however other examples of inductive communication technology that could be used include a passive low frequency interface (PaLFI) device which operates at approximately 135 kHz, such as the TMS37157 Target Board available from Texas Instruments, Dallas Tex., USA, or other radio frequency identity (RFID) devices, e.g. operating at a frequency of 125 kHz. Inductive power transfer can operate at a variety of frequencies. Other standard protocols may operate in the range of 100-200 kHz. Frequencies both above and below this range can be contemplated, with a chosen frequency being some balance between regulatory restrictions, biological interactions and efficiency of energy transfer.

Electrodes 30 may be located along an exterior surface of housing 34 and are coupled to pulse generator 28 via insulated feedthroughs. In other embodiments, electrodes 30 may be carried by a lead or insulated tether electrically coupled to pulse generator 28 via appropriate insulated feedthroughs or other electrical connections crossing sealed housing 34. In still other embodiments, electrodes 30 may be incorporated in housing 34 with externally exposed surfaces adapted to be operably positioned in proximity to a targeted nerve and electrically coupled to pulse generator 28.

Figure 3:
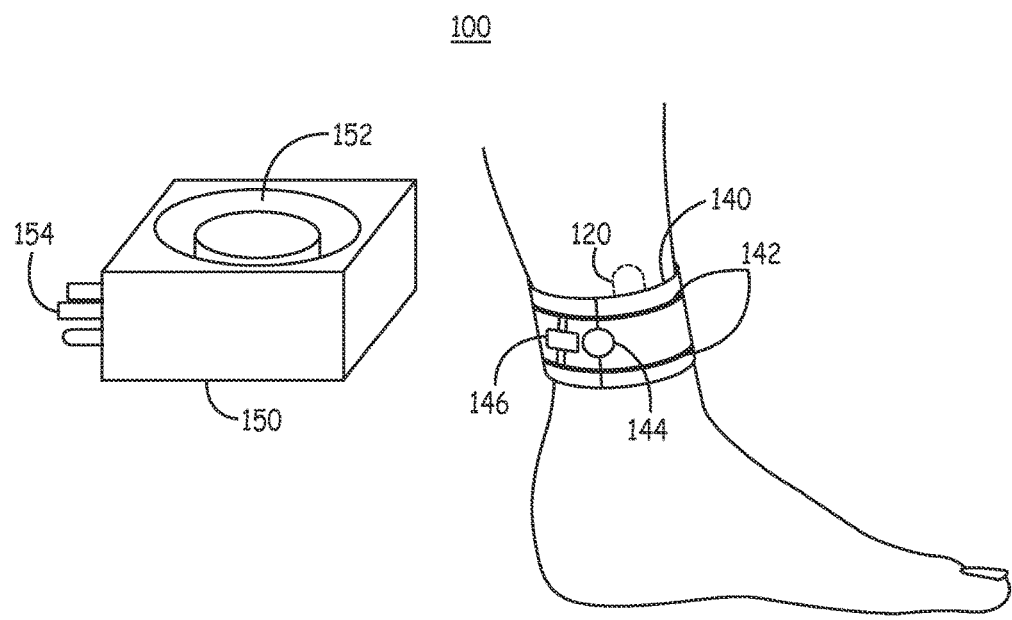
FIG. 3 is a schematic diagram of one exemplary embodiment of an implantable neurostimulation (INS) system including an IMD, external device, and charging unit.

FIG. 3 is a schematic diagram of one embodiment of an INS system 100 including an IMD 120, external device 140, and charging unit 150. IMD 120 is an externally powered device or may include a rechargeable battery cell or other rechargeable energy storage device. As such, IMD 120 includes an electrically conductive coil (not shown in FIG. 3) configured to be inductively coupled to an external coil 142 included in external device 140 for inductive power transfer from external device 140 to IMD 120.

External device 140 is shown as a wearable device, which is an ankle cuff in the illustrative embodiment, for electromagnetic coupling and inductive power transfer to an IMD 120 implanted along the medial portion of a patient's ankle for delivering an electrical stimulation therapy to the tibial nerve to treat overactive bladder syndrome. It is recognized, however, that the apparatus and techniques described herein may be implemented or adapted for use in a wide variety of IMD systems. The shape and contour of external device 140 may be adapted for a secure and comfortable fit at a particular body location. For example, when positioned around the ankle, external device 140 may include a recess or curve to avoid pressure or contact between the external device 140 and the medial malleolus (inner ankle bone) to prevent patient discomfort.

External device 140 includes a power source 146, which is a rechargeable power source in the illustrative embodiment shown, coupled to at least one primary coil 142 for transferring power from external power source 146 to IMD 120. External device 140 includes electrical contacts for electrically coupling to charging unit 150 for recharging power source 146. Charging unit 150 includes an electrical plug 154 for plugging into a wall socket for recharging power source 146 using a standard 110V or 220V outlet for example. Charging unit 150 includes a receptacle 152 configured for receiving and retaining external device 140 during charging. Charging unit 150 and external device 140 may be configured with mating geometries including curves, ridges, grooves, varying internal and/or external diameters or other features to promote proper positioning and electrical connection of external device 140 with charging unit 150.

External device 140 is shown in FIG. 3 as a cuff but may be implemented as a variety of wearable structures such as a sock or a boot. In other embodiments, as described further below, external device 140 is provided as a sleeve or appliance in which a patient positions a foot, ankle, leg, arm, hand, wrist, or other body part corresponding to an implant location of IMD 120 to establish an electromagnetic field for inductive power transfer.

The external device 140 may include an adjustable fit device 144, which enables the patient or caregiver to adjust the fit of the external device around the patient to reduce a distance from and improve inductive coupling between a primary external coil 142 and an internal coil. In some embodiments, adjustable fit device 144 is a button actuated air pump that inflates at least a portion of external device 140 to provide a snug fit around the patient. In other embodiments, an adjustable button, clip, clasp, buckle or other fastener, a metal or polymeric "slap-on" band, elastic or shape memory material, or any combination thereof may be used to provide an adjustable or conformable fit of external device 140 to a desired body portion of the patient.

One challenge faced in providing an externally powered or rechargeable IMD 120 is ensuring adequate positioning of an external coil 142 relative to the implanted coil of IMD 120 for efficient power transfer. IMD 120 may be miniaturized in a minimally invasive system and therefore accurate positioning of an external coil over IMD 120 may be challenging. IMD 120 may migrate over time or shift with patient movement causing a change in the relative positioning of IMD 120 and external device 140.

In the embodiment shown, external device 140 includes a coaxial pair of electrically conductive coils 142 spaced apart along external device 140 and encircling the patient's ankle Coils 142 are wound in the same direction and electrically coupled in parallel to power source 146 and will provide a uniform electromagnetic field in the patient's ankle for inducing current in the implanted coil to thereby transfer power to the IMD 120. Two or more coils extending around the patient's ankle (or other body part) may be used for generating a uniform electromagnetic field over a desired surface area of the patient's body to encompass a likely location of IMD 120. By providing a uniform electromagnetic field over a relatively larger portion of the patient's body than the IMD 120 and encompassing a likely location of the IMD 120, the patient's burden in properly aligning or positioning external device 140 can be reduced.

Figure 4:
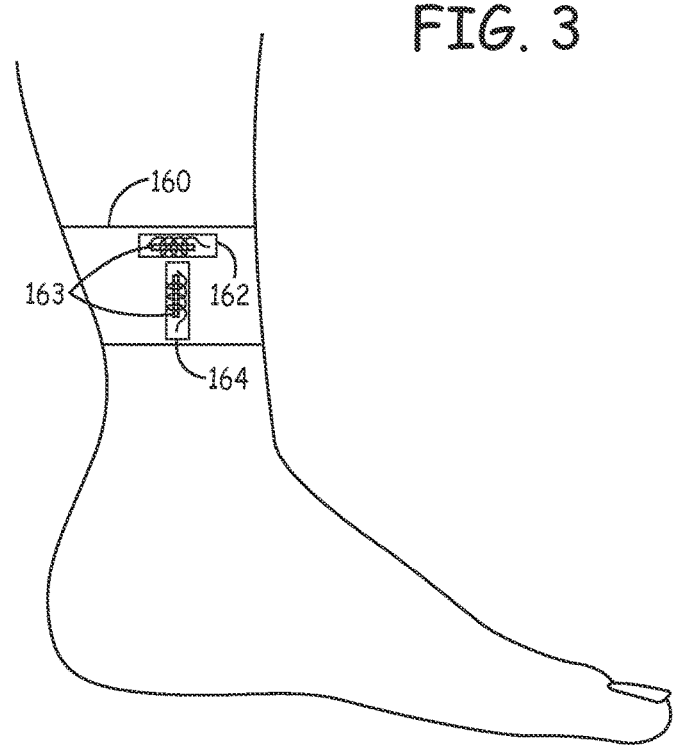
FIG. 4 is a schematic diagram of an exemplary external device including one or more coils having ferrite cores as opposed to the air core coils as shown in FIG. 3.

FIG. 4 is a schematic diagram of an external device 160 including one or more coils 162 and 164 having ferrite cores 163 as opposed to the air core coils 142 shown in FIG. 3. A ferrite core can enhance the electromagnetic field produced by the coil 162 or 164. Two or more coils 162 and 164 may be arranged in a one-dimensional or two dimensional array along external device 160 and tested independently to determine which coil has the best coupling with the implanted coil based on a power feedback signal as will be described in greater detail below. The coils 162 and 164 may be arranged in parallel or at an angle such as the approximate perpendicular angle as shown in FIG. 4.

Figure 5:
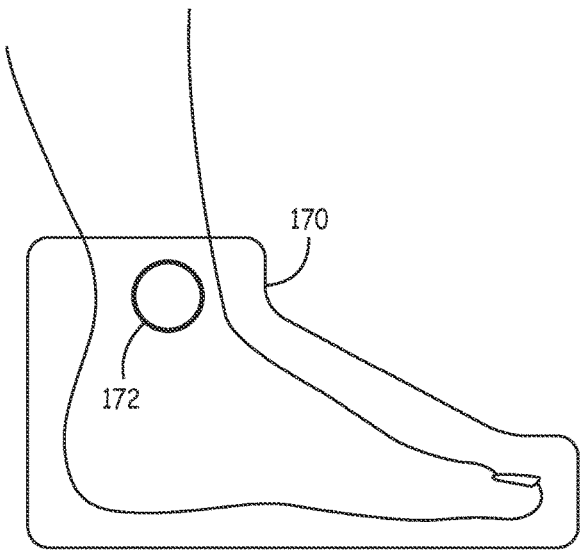
FIG. 5 is a schematic diagram of an exemplary alternative embodiment of an external device including a coil for inductive power transfer to an IMD.

FIG. 5 is a schematic diagram of an alternative embodiment of an external device 170 including a coil 172 for power transfer to an IMD. External device 170 may be a wearable device that allows a patient to be ambulatory, much like a sock or a boot, or may be a stationary boot-like appliance that the patient inserts a foot into during a recharging or therapy delivery session to maintain electromagnetic inductive coupling between the external coil 172 and an implanted coil. In the example shown, a circular coil 172 is shown positioned along the device 170, e.g. along an interior surface of the device or embedded within the device, in a position that results in approximate alignment with an implanted coil. Numerous external coil configurations could be implemented in a wearable external device or appliance used for transferring power to the IMD and other examples will be described and illustrated herein.

Figure 6A:
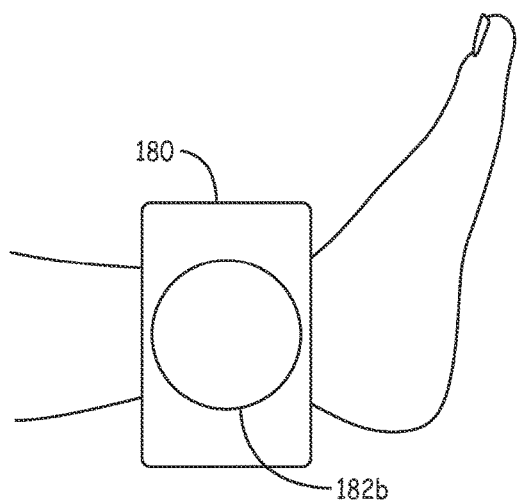
FIG. 6A and FIG. 6B show a side and end view, respectively, of an exemplary external device configured as an appliance in which the patient rests or positions a body portion to align an implanted coil with an external coil included in the external device.
Figure 6B:
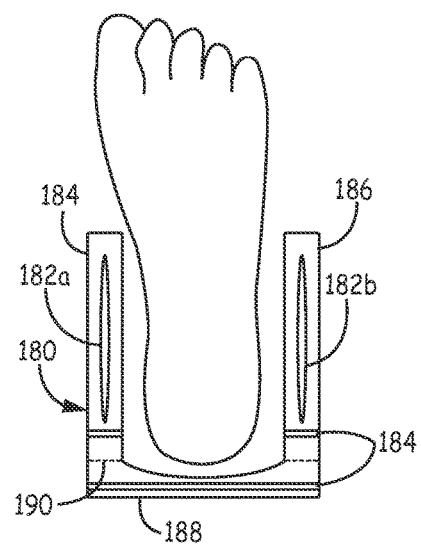

FIG. 6A and FIG. 6B show a side and end view, respectively, of an external device 180 configured as an appliance in which the patient rests or positions a body portion to align an implanted coil with an external coil included in the external device 180. The external device 180 may be sized and contoured to provide a comfortable fit for the patient and for accommodating anatomical features.

The external device 180 includes one or more primary coils 182a, 182b for transmitting power to the implanted device via inductive coupling with an implanted coil. In the illustrative embodiment of FIG. 6B, two coaxial circular coils 182a and 182b are shown positioned along a medial wall 184 of the external device 180 and along a lateral wall 186 of the external device such that the patient's ankle is positioned between the coaxial coils 182a and 182b. In this way, a uniform electromagnetic field is induced between the coils when coils 182a and 182b are wound in the same direction and driven in phase by an applied current. The uniform electromagnetic field promotes efficient current induction in a coil of the associated IMD implanted in the medial portion of the patient's ankle for stimulating the tibial nerve in this example.

The external device 180 may include a passive or active cooling system 184 to prevent overheating of the external device 180 during power transfer, which might otherwise cause patient discomfort. In the embodiment shown, cooling system 184 is a passive cooling system including a network of fluid channels 184 that allow heat to be conducted away from the patient. In alternative embodiments, heat absorbing materials may be incorporated along an outer portion of external device 180, such as a wax or other phase change material (PCM) to provide heat sinks away from the patient. Active cooling systems could include fluid pumps that circulate air or another fluid through a system of channels formed in external device 180. Heat management techniques in external device 180 may include any active and/or passive cooling techniques and/or insulation. Among other heat management techniques that may be used are Peltier cooling elements, external ice/cold packs, fans, thermally conductive and insulation material/members.

External device 180 may be a foldable device for packing and storing for convenience. For example, medial wall 184 and lateral wall 186 may be coupled to base 188 at rotatable hinges 190 allowing walls 184 and 186 to be folded down on base 188 when not in use. External device 180 may be a battery powered device or powered using a standard 110V or 220V outlet. In some embodiments, external device 180 includes a rechargeable cell or energy storage device that is recharged by plugging external device into a standard 110V or 220V outlet, directly or via a charging unit as described above.

FIGS. 7-11 are schematic diagrams of alternative embodiments of an external electrically conductive coil included in an external device for inductive power transfer to an IMD. The various embodiments of external coils described herein may be incorporated in a wearable external device such as a cuff, boot, sock or clip-on type device or an external device intended for stationary use such as a boot, stand or appliance like the external device shown in FIGS. 6A and 6B. Each of the various coil shapes may be implemented singly or in any combination, including ordered linear or circular arrays, random, concentric or opposing arrangements. The coils may be printed on a printed circuit board or flexible substrate or other conformable electronic substrate or be wound and mechanically coupled to a surface or embedded within layers of the external device. Examples of conductive materials that may be included in an external or implantable coil in various embodiments herein include those comprising copper, nickel, gold, platinum, niobium, tantalum, titanium, alloys thereof or alloys such as MP35N or titanium alloyed with molybdenum, and the like. Materials may be inherently biostable/biocompatible, or they may be clad with biostable/biocompatible materials (such as silver cored wire clad with MP35N) or may be coated, overmolded or potted with polymeric or ceramic material, or enclosed in a hermetic or sealed enclosure.

Figure 7:
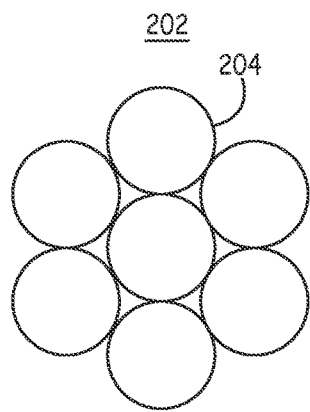
FIG. 7 depicts an exemplary two-dimensional array of electrically conductive coils for inductive power transmission.

FIG. 7 depicts a two-dimensional array 202 of coils 204 which are each shown of equal size in FIG. 7, but may alternatively vary in size. In the various embodiments shown in FIGS. 7-11, individual external coils are generally larger in diameter than the IMD itself. Typical sizes may range from approximately a half inch to several inches in diameter, with sizes between one to three inches perhaps being most common. An external coil configuration for use in power transmission as described herein is not intended to be limited to any particular coil size, however. Optimal inductive coupling is generally achieved when a primary coil radius is approximately 1.4 times the distance to the secondary coil. To illustrate, if an implanted coil is between 1 and 2 cm beneath the skin, an external air core coil may have a diameter in the range of approximately 1 to 2.5 inches. Different embodiments may require larger coils depending on the depth of an implanted coil beneath the skin and the proximity of an external coil included in an external device to the skin when properly positioned for power transmission. When multiple concentric coils or coil arrays are included, the coil sizes may range in size. A number of windings included in a coil can vary depending on a chosen carrier frequency and may range between one turn and more than 100 turns.

The coils 204 are shown as air-core, circular coils or loops arranged in a circular array. In alternative embodiments, coils of the same or varying size may be arranged in a linear, rectangular or circular array of coils with or without a ferrite core. Coils arranged in a two-dimensional array along the external device may be linear coils, coils shaped into a circle (as shown in FIG. 7), polygonal, spiral or other shapes. The two dimensional array promotes optimal coupling with an implanted coil over a range of horizontal and vertical positions of the external device to mitigate misalignment of an external device with the IMD.

The coils 204 may be coupled to a drive signal source independently, all simultaneously or in any combination. When driven independently or in different combinations, a power transfer feedback signal received from the IMD may be used to select one or more coils 204 providing the highest or most efficient power transfer. The use of a power transfer feedback signal for optimizing coupling between one or more external coils and an implanted coil will be described in greater detail below.

Figure 8:
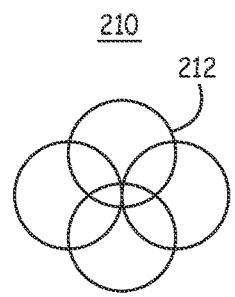
FIG. 8 depicts an exemplary two-dimensional coil array of overlapping coils.

FIG. 8 depicts a two-dimensional coil array 210 in which coils 212 are overlapping. Similarly to the array of FIG. 7, the coils 212 may be operated independently or in any combination to achieve optimal coupling for power transfer to an IMD. The coils 212 may be circular or polygonal loops or linear coils and may have air or ferrite cores.

Figure 9:
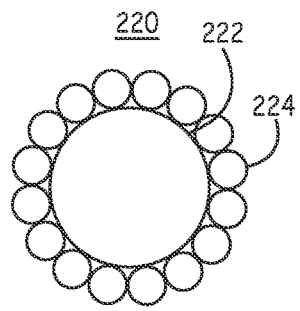
FIG. 9 depicts an exemplary circular array of differently sized circular coils.

FIG. 9 is a circular array 220 of differently sized circular coils 222 and 224. A relatively large center coil 222 is circumferentially surrounded by relatively smaller circular coils 224. The smaller coils 224 may be tested independently one at a time and a power transfer feedback signal may be used to identify which of the smaller coils 224 is optimally aligned with the implanted coil. This location of the optimally aligned coil is used to provide directional feedback to the patient or a caregiver for adjusting the position of array 220 relative to the IMD. Once the array 220 is optimally positioned, any one or combination of coils may be used for power transfer. For example, relatively larger coil 222 may be used alone, or, if optimally positioned, a smaller coil 224 may provide more efficient power transfer.

Figure 10:
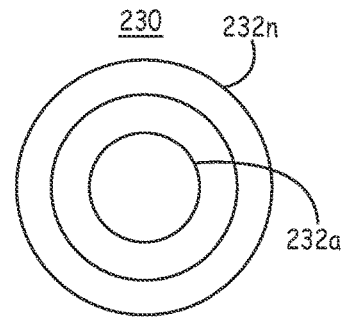
FIG. 10 depicts an exemplary concentric array of n circular coils.

FIG. 10 is a concentric array 230 of n circular coils 232*a* through 232*n*. The concentric coils may be selected one at a time to determine proximity to the implanted coil. Adjustment of the position of array 230 may be made based on a power transfer feedback signal. The concentric coils 232*a-n* may then be selected in any combination for optimal coupling during power transfer. For example, the smallest coil having the best coupling may be selected for the most efficient power transfer.

Figure 11A:
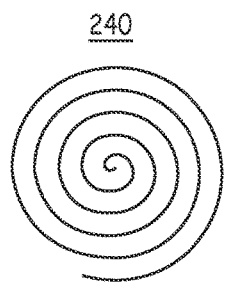
FIG. 11A, 11B, and 11C depict exemplary shapes of a spiral coil that may be used individually, in a concentric pairs, or in an arrays of coils in an external device.
Figure 11B:
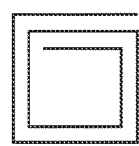
Figure 11C:
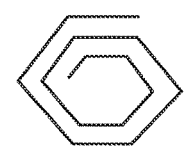

FIG. 11A is a spiral coil 240 that may be used individually, in a concentric pair, or in an array of coils in an external device. The spiral coil 240 may be circular as shown or have a polygonal spiral shape, such as a spiraling square as shown in FIG. 11B or hexagonal shape as shown in FIG. 11C for example. The spiral coil 240 may be printed on a circuit board or flexible substrate.

Figure 12:
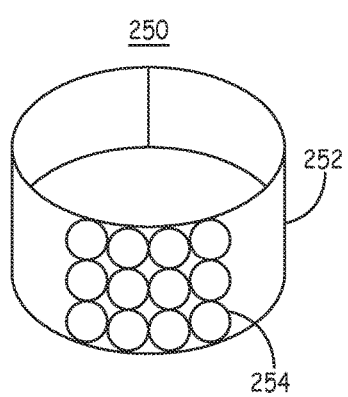
FIG. 12 is a schematic diagram of an exemplary external device including a wearable cuff carrying a two-dimensional array of circular or ring coils.

FIG. 12 is a schematic diagram of an external device 250 including a wearable cuff 252 carrying a two-dimensional array of circular or ring coils 254. As described above, each of the coils 254 in the array may be controlled independently to identify a coil having optimal coupling to an implanted coil. This information can be used as feedback for adjusting the position of cuff 252 and/or in selecting one or more of coils 254 for applying a drive signal for inducing an electromagnetic field. The array shown in FIG. 12 is arranged in a two-dimensional rectangular array on a conformable or contoured wearable cuff. In other embodiments, multiple coils may be arranged in a one-dimensional linear array extending vertically, horizontally or at any angle along cuff 252. The coils may be embodied as any of the coil configurations described herein.

Figure 13:
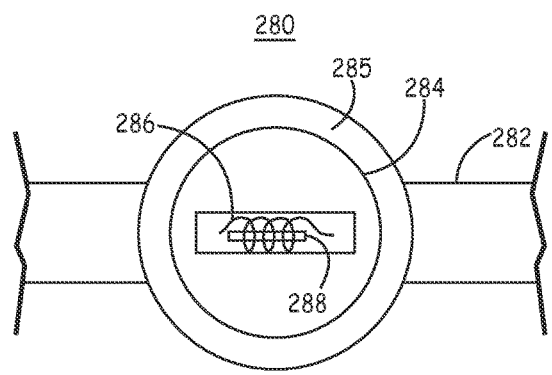
FIG. 13 is a schematic diagram of an exemplary alternative embodiment of an external device including a wearable cuff, a rotatable dial and a linear coil.

FIG. 13 is a schematic diagram of an alternative embodiment of an external device 280 including a wearable cuff 282, a rotatable dial 284 and a linear coil 286. Coil 286 is wound on a ferrite core 288. The angular orientation of linear coil 286 relative to an implantable coil may be adjusted by rotating dial 284. In some embodiments, dial 284 is a clip-on device that may be attached to cuff 282, or optionally to any garment the patient is wearing over the location of the IMD. The angular orientation may be adjusted until optimal power transfer is achieved, for example based on a power transfer feedback signal. The rotatable dial may include pre-determined positions established by interfacing stops configured between the dial and a face plate 285 that the rotatable dial 284 is mounted on such that the degree of rotation of the dial is controlled. In some embodiments, dial rotation and selection of dial position for power transmission could be an automated process controlled by a control module receiving the power transfer feedback signal and configured to control an actuator or motor for turning dial 284.

Figure 14:
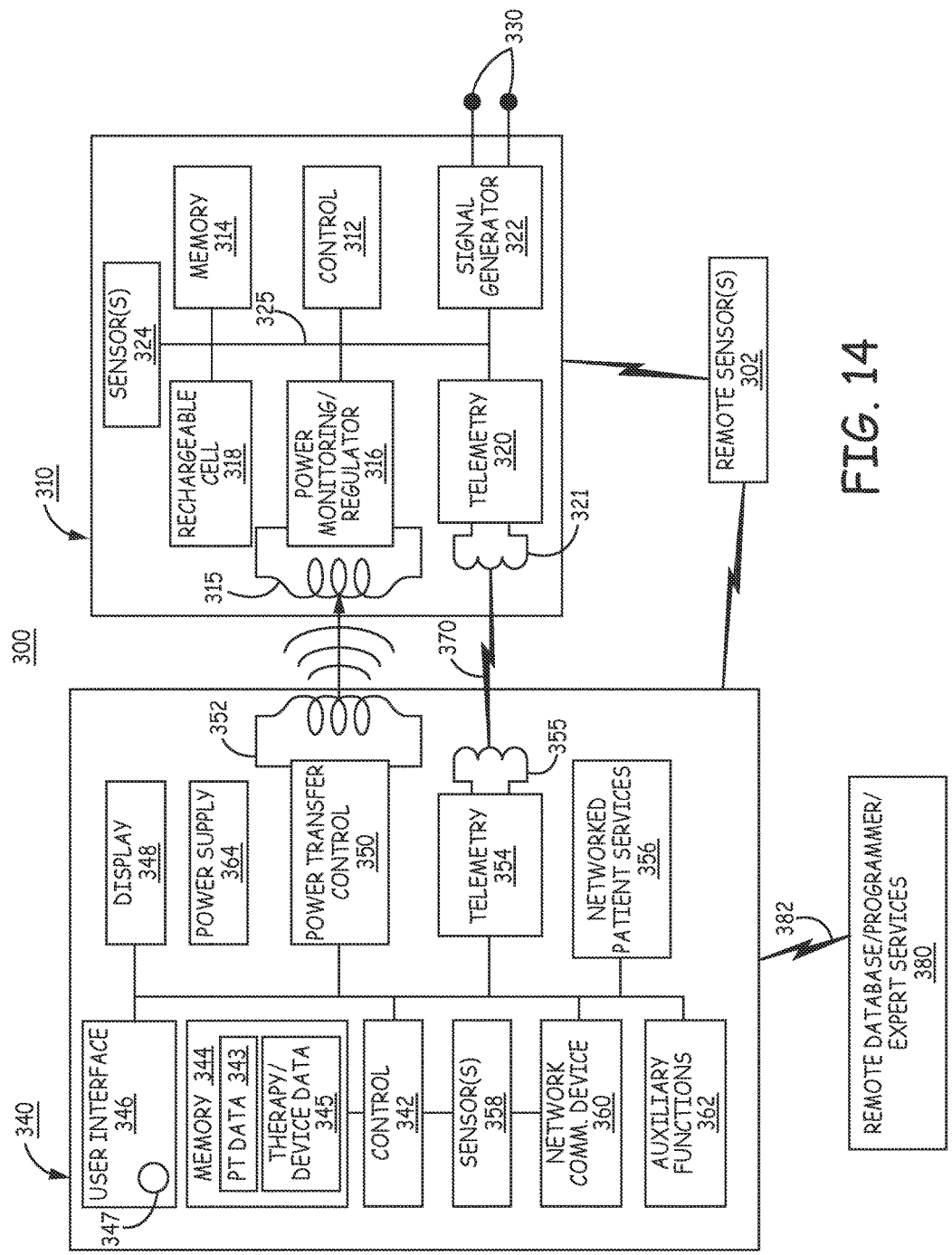
FIG. 14 is a functional block diagram of an IMD system according to one exemplary embodiment.

FIG. 14 is a functional block diagram of an IMD system 300 according to one embodiment. IMD system 300 includes an IMD 310, an external device 340, a remote sensing device 302, and a remote database/programming device 380. IMD 310 includes controller 312 and associated memory 314, a power monitoring and regulator module 316 and associated implantable secondary coil 315, a telemetry module 320 and associated antenna 321, and signal generator 322 coupled to at least one pair of electrodes 330. IMD 310 may include a charge storage device 318 and one or more sensors 324.

Controller 312 controls IMD functions and may be implemented as a microprocessing device executing instructions and using operating parameters stored in memory 314. Signal generator 322 receives a regulated voltage signal from power monitoring and regulator module 316 and/or charge storage device 318 for generating a therapeutic electrical signal delivered to a targeted therapy site via electrodes 330. Telemetry module 320 is used for bidirectional communication with external device 340 and may be used to receive signals from one or more remote sensors 302.

Power monitoring and regulator module 316 is coupled to a secondary coil 315 that is inductively coupled to external coil 352 of external device 340 when a drive signal is applied to external coil 352. Power transmission is performed by inductive coupling between implanted coil 315 and external coil 352. External coil 352 may be implemented according to any of the coil configurations described herein. Power monitoring and regulator module 316 measures the power transmitted from external device 340 or a signal correlated to the inductively coupled signal and generates a power transfer feedback control signal transmitted via telemetry 320 back to external device 340. As further described below, this feedback signal is used by external device 340 to control a drive signal applied to external primary coil 352 to control and optimize the power transfer. In some embodiments, power transmission via inductive coupling between antennas using a Near Field Communication (NFC) signal or other inductive communication technique is performed. Methods described herein for using a power transmission feedback signal may be adapted for use with any inductive power transmission technique.

Power monitoring and regulator module 316 may provide a rectified voltage output signal to signal generator 322. Signal generator 322 uses the rectified voltage signal to generate stimulation output signals. A pulse amplitude, pulse width, pulse frequency or other stimulation control parameter may be adjusted by controller 312 or signal generator 322 in response to the received amplitude or signal pattern of the inductively coupled signal.

The inductively coupled signal may also be used to provide power to controller 312, telemetry module 320 and other IMD circuitry. A data bus 325 couples IMD components and carries an output signal from power monitoring and regulator module 316 to other IMD components. In this way, power monitoring and regulator module 316 may provide inductively received power for all or any portion of IMD functions. IMD 310 may include a charge storage device 318, e.g. a rechargeable cell, capacitor or supercapacitor, for storing power transferred from external device 340 to IMD 310 through inductive coupling, in which case power monitoring and regulator module 316 provides a rectified voltage output signal to charge storage device 318. Charge storage device 318 may be used to provide power to any other IMD circuitry components requiring a voltage input signal.

A feedback control signal is correlated to the inductively coupled signal and is generated by power monitoring and regulator module 316 by measuring the inductively coupled signal received from implantable coil 315, measuring an output signal from regulator module 316, measuring a therapeutic electrical stimulation signal output from signal generator 322, and/or measuring a physiological sensor signal measuring a response to the electrical stimulation. As such, a signal output measurement from signal generator 322 may be carried back to power monitoring and regulator module 316 via data bus 325. The feedback control signal is transmitted to external device 340 by telemetry module 320 via link 370 and used by external device 340 to control and optimize power transfer for charging a charge storage device 318. The feedback control signal may correspond to an amplitude of a rectified Vout signal from power monitoring and regulator module 316 and/or the amplitude of a therapy signal output from signal generator 322. The external device 340 can adjust a drive signal applied to external coil 352 up or down to adjust the transmitted power, i.e. the inductively coupled signal induced in coil 315, accordingly.

IMD 310 may include one or more sensors 324 for use in detecting a need for therapy delivery, monitoring a response to therapy delivery, controlling therapy delivery on/off times, and/or providing feedback to a patient to indicate that re-positioning of external device 340 and/or the patient's body is required. In some embodiments, a physiological response signal may be used by external device 340 to adjust a power transmission signal. Among the sensors that may be included in sensors 324 are electrodes for sensing an electromyogram (EMG) signal and/or a nerve signal, an activity or motion sensor, a posture sensor, and an acoustical sensor.

External device 340 includes, controller 342 and associated memory 344, a user interface 346, display 348, power transfer control module 350 and associated primary coil 352, telemetry module 354 and associated antenna 355, networked patient services module 356, sensors 358, a network communication device 360 and auxiliary functions module 362. A power supply 364, which may be a rechargeable or primary cell, provides power to the external device circuitry.

The functionality described and attributed to external device 340 may be implemented in a single external device or may be distributed across two or more external devices enabled for telemetric communication with each other or with other system components in order to seamlessly provide the described functionality. For example, some of the functions attributed to external device 340 shown in FIG. 14 may be implemented in a patient handheld device while other functions are implemented in a wearable external device.

Power transfer control module 350 transmits power through inductive coupling between external coil 352 and implanted coil 315. In some embodiments, the power transmission signal, i.e. a drive signal, is applied to external coil 352 in a pattern, e.g. frequency, amplitude and/or duty cycle, that establishes stimulation control parameters such as pulse amplitude, pulse width, pulse frequency and/or duty cycle. In this way, the power transmission signal is used to provide power to IMD 310 and to set the stimulation control parameters instead of programming therapy control parameters into IMD 310. Therapy control is achieved by adjustment of the power transmission signal rather than by the implanted device itself. For example, if the external device 340 transfers bursts of power at a therapy pulse rate, with a therapy pulse width, and with some relative therapy delivery amplitude, the IMD 310 could rectify the power signal and deliver it directly to the electrodes. In this way, the IMD 310 is nearly fully passive, and all the therapy control is implemented in the external device 340 by controlling the power transmission signal.

External device 340 receives a power transfer feedback signal from power monitoring and regulator module 316 via telemetry link 370. In some embodiments, power transfer control module 350 adjusts a drive signal applied to coil 352 in response to the feedback signal. The drive signal may be increased or decreased to control a desired level of power transmission while minimizing the power expended by external device 340.

The power monitoring and regulator module 316 generates a DC voltage that is proportional to the power that is transferred. The signal generator 322 is functions like a switch that gates the DC voltage to the electrodes 330, creating a stimulation pulse. By measuring the DC voltage, which is proportional to the transferred power, and providing a feedback signal to the external device 340 indicating the DC voltage amplitude, the transferred power can be increased or decreased as needed to control the DC voltage to maintain a desired stimulation voltage delivered to electrodes 330. The DC voltage measurement point can be at the output of power monitor/regulator 326 or the stimulation pulse amplitude output by signal generator 322.

Variation in the transferred power, e.g. due to variation in the placement of the external controller 340, and changes in programmed stimulation voltage amplitudes can all be controlled in one feedback loop. The feedback signal can be based on a DC signal measurement as described above or a physiological sensor signal from sensors 324, sensors 358, or remote sensors 302 that measures a physiological response, such as EMG or muscle motion due to nerve capture or actual nerve fibers firing due to stimulation. The feedback signal is then used to control the power transmission to achieve a desired physiological response Alternatively, the power transfer feedback signal may be used by control 342 to control display 348 to generate a display to a user to indicate the power transfer efficiency. The power transfer efficiency may be reduced when the external device 340 is not optimally positioned for inductive coupling between external coil 352 and implanted coil 315. A user may adjust the position of external device 340 or adjust a position or orientation of a body part relative to external device 340 until display 348 indicates an improved or optimal power transfer efficiency. Display 348 may indicate the power transfer efficiency by way of an LED display, e.g. a number of LEDs illuminated relative to a total number of LEDs not illuminated indicates a relative power transfer efficiency, an audible signal, text signal, visible icon, or other user perceptible signal. By maximizing the power transfer efficiency, the drain on power supply 364 can be reduced, increasing longevity of a primary cell in the external device 340 or increasing time between or reducing the number of recharges of a rechargeable cell in the external device 340. Various methods for controlling power transfer with the use of a power transfer feedback signal will be further described below.

External device 340 includes a user interface 346 which may enable a patient to manually adjust stimulation control parameters or turn external device 340 on and off. In one embodiment, user interface 346 includes a therapy activation button 347 that enables a patient to manually start a stimulation therapy or stop a stimulation therapy that is already in progress.

User interface 346 may additionally be used by the patient to enter patient data, such as patient diary information relating to symptoms or events associated with the treated condition and therapy being delivery. In the example of tibial nerve stimulation for treating overactive bladder syndrome, a patient may enter fluid intake, voiding times, wetting events, medications taken, or other data. Display 348 may prompt the patient at regular intervals to enter patient diary data. Alternatively display 348 may prompt the patient to enter data when an expected data entry has not been received. Memory 344 may store patient data 343 entered by the patient or automatically acquired by external device sensors 358 and/or remote sensors 302.

In some embodiments, external device 340 includes one or more sensors 358 for providing feedback signals that may be used in optimizing power transmission and/or acquiring patient and therapy related data. Sensors 358 may include electromyogram (EMG) sensing electrodes, an activity sensor, and/or a postural sensor though other sensors may be used depending on the information relevant to a particular therapy application.

EMG sensing electrodes may be used to provide a signal to controller 342 and/or power transfer control 350 for use in controlling power transferred to IMD 310. The EMG signal response may be used to control the amplitude of delivered power that in turn controls the amplitude of delivered therapeutic electrical stimulation pulses. By increasing or decreasing the transferred power signal, by adjusting the drive signal applied to external primary coil 352, the therapy pulse amplitude may be increased or decreased and the result on the stimulated nerve is monitored by measuring a feature of the EMG signal. An EMG signal may be acquired using implanted or external (surface) electrodes, and EMG sensing may be performed during delivery of a stimulation pulse.

Additionally or alternatively, the EMG signal may be used to monitor and quantify therapy delivery time intervals, e.g. times of day of therapy delivery, frequency of therapy delivery, duration of therapy delivery intervals, and total time that therapy is delivered cumulatively or over a predetermined time interval such as daily or weekly. This therapy delivery data may be stored in therapy/device data 345 of memory 344 and transmitted to remote database/ programmer 380 for use by a clinician in evaluating therapy effectiveness, assessing patient compliance, and making adjustments to a therapy protocol as needed.

An EMG signal (or another sensed signal that varies in response to therapeutic stimulation) may be transmitted to a patient hand-held device in some embodiments to provide a patient a feedback display of therapy activity. The patient will be aware therapy is in progress and efficacious stimulation pulses are being delivered. This allows a patient to stop a therapy in progress if needed, adjust therapy delivery parameters if desired, and may simply provide reassurance to the patient that therapy is being delivered effectively.

A posture sensor, e.g. a 3-dimensional accelerometer, included in sensors 358 may be used to determine the position, e.g. upright, prone, semi-prone, left-lying, right-lying, etc., of the patient's body portion on which external device 340 is positioned. In some cases, the body position may influence the position of the IMD 310 relative to the external device 340, which may affect power transfer efficiency. Body position may also influence the relative position of electrodes 330 to a target nerve. Accordingly, body position may be monitored using a posture sensor, included in implanted sensors 324 or external sensors 358. Feedback to the patient to adjust body position may be provided via display 348 as required.

An activity sensor, which may be embodied as an accelerometer or piezoelectric crystal, or other motion sensor included in sensors 358 and/or 324 may be used to sense muscular motion caused by therapy delivery and used as a therapy delivery feedback signal, similar to the use of an EMG signal as described above.

Alternatively, an activity sensor may be used in controlling therapy delivery by stopping or starting therapy delivery based on an activity signal. When a patient activity is detected that corresponds to an activity state during which therapy delivery is undesirable, therapy may be stopped. Depending on the target site and therapy intensity, therapy delivery may cause altered motor activity that could be undesirable during certain patient activities, such as operating a motor vehicle, walking, jogging, running, stair climbing, cycling etc.

Accordingly, controller 342 may be configured to perform an activity sensor signal analysis for detecting and discriminating between activity states and automatically inhibit or enable therapy delivery according to activity state. At times, therapy delivery may be automatically inhibited to avoid undesired motor activity during a particular patient activity. At other times, when a patient activity is detected during which therapy is desired, such as a resting state, therapy delivery may be automatically enabled. In still other cases, an activity sensor signal may be analyzed to detect a particular pattern of a patient movement performed intentionally by the patient to start or stop therapy delivery.

In one embodiment, the external device is configured to position the external primary coil for inducing an electromagnetic field along a region of the tibial nerve, e.g. as shown in FIGS. 3-6 for example. The IMD having associated electrodes is adapted to deliver therapeutic electrical stimulation signal to the tibial nerve, for example through a deep fascia tissue layer, superior to the flexor retinaculum. A detected activity state that corresponds to an intrinsic activation of the tibial nerve, stair climbing or driving an automobile, may cause a drive signal applied to the external coil to be withheld to inhibit the therapeutic electrical stimulation in response to the detected activity state.

As mentioned previously, IMD 310 may include one or more sensors 324. Accordingly, acquiring a sensor signal, analysis of a sensor signal, and control of IMD operation based on the sensor signal as generally described above with regard to external sensors 358 may all or in part be implemented in IMD 310 or based on an implanted sensor signal being transmitted via telemetry unit 320.

External sensors 358 may include a camera positioned to provide a visualization of the positioning of external device 340 relative to a patient's body, e.g. relative to an anatomical marker such as the medial malleolus. A camera image may be transmitted via a networked communication device 360 to remote database/programmer/expert services 380 to enable a remote technician or clinician to aid a patient in trouble-shooting when power transmission or communication between external device 340 and IMD 310 is not optimized.

External device 340 includes a network communication device 360 to enable communication between external device 340 and other devices on a wired or wireless network, e.g. a personal area network (PAN), body area network (BAN), body sensor network (BSN), local area network (LAN) or a wide area network (WAN), such as a WiFi wireless technology network, BLUETOOTH® wireless technology network, or ZIGBEE® wireless technology network. For example, external device 340 may communicate with remote database/programmer/expert services 380 via communication link 382 for transferring data from memory 344 or in real time to enable a clinician or technician to evaluate patient data, therapy data, or device related data (such as battery life) for programming external device 340 and/or IMD 310 remotely, prescribing therapy protocol adjustments or giving other patient care instructions.

External device 340 may include a networked patient services module 356 configured to perform services for the patient such as aiding in troubleshooting, providing social connectedness such as linking the patient to other patients or experts in a help line or chat line type of format, locating restroom facilities, providing patients with incentives for compliance, or other services related to the treated patient condition but somewhat peripheral to the therapy delivery itself.

External device 340 may include auxiliary functions module 362 that provides added functionality in a multi-use device that may be unrelated or indirectly related to the therapy delivery itself. For example, auxiliary functions module 362 may include a pedometer to provide exercise monitoring or other functionality that relates to patient wellness.

In other embodiments, system 300 may include one or more remote sensors 302 configured to transmit a sensor signal to IMD 310 and/or to external device 340 for use in controlling IMD function and/or accumulating patient or therapy related data. A remote sensor may be used to detect a need for therapy and/or a therapeutic response at a target organ. Remote sensor(s) 302 may include implanted and/or external sensors. For example, in the application of tibial nerve stimulation for treating overactive bladder syndrome, a remote sensor 302 may be implanted for sensing bladder activity, bladder volume or another indication of a likely urge event. The remote sensor may transmit a signal continuously to the IMD 310 for analysis by controller 312 or transmit a signal that an event or condition warranting a change in therapy is detected. In response, controller 312 may control IMD 310 to start, stop or adjust therapy intensity (e.g. increase or decrease a pulse amplitude, pulse width, pulse frequency, duty cycle or other therapy control parameter).

Remote sensor(s) 302 may transmit a signal to external device 340 for accumulating patient or therapy-related data for assessing therapy effectiveness and compliance and/or for use by controller 342 and/or power transfer control 350 in controlling IMD therapy delivery functions. Remote sensors 302 may include a posture sensor, activity sensor, acoustical sensor, pressure sensor, EMG sensor, nerve activity sensor, impedance sensor, volume sensor or the like.

In some embodiments, system 300 is configured to characterize a patient's urinary urge pattern to enable the system 300 to automatically control signal generator 322 to optimally deliver therapy to alleviate the intensity and/or frequency of urges and/or prevent urge incontinence. Characterization of a patient's urge pattern may be performed by controller 342 and/or remote database/programmer/expert services 380 using input stored in patient data 343 and therapy/device data 345, which may include patient data input by the patient, sensor signal data, and therapy delivery data. In this way, the therapy delivery may be optimized to achieve maximum benefit to the patient while conserving power and avoiding patient inconvenience and burden.

Figure 15:
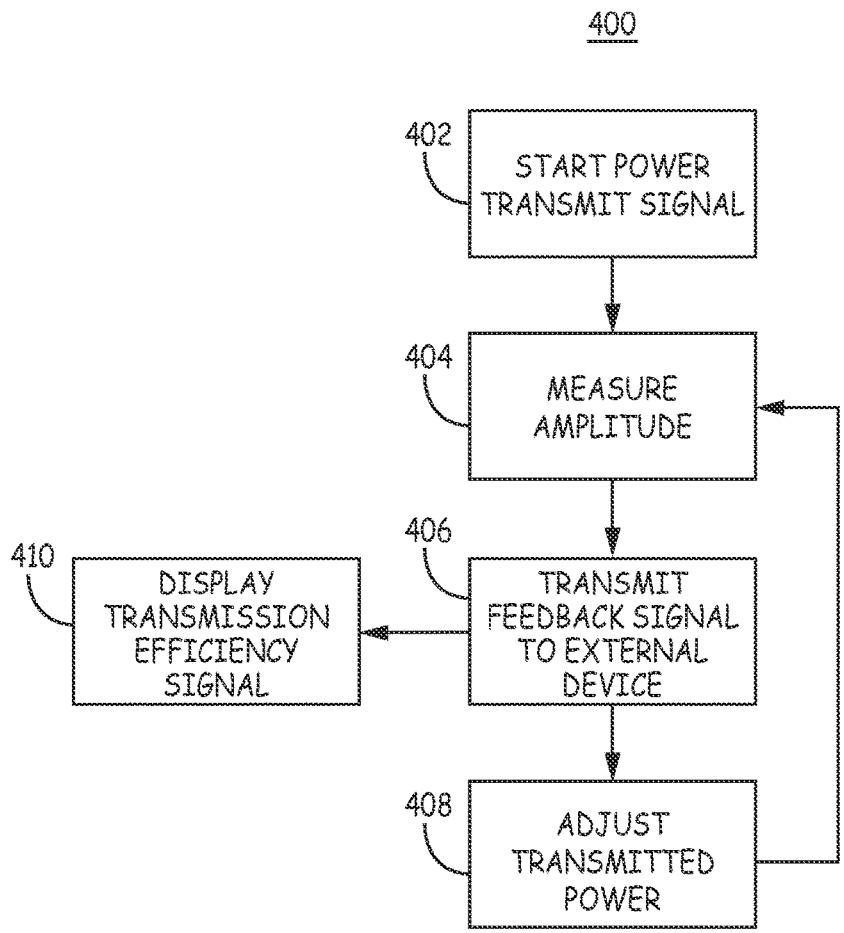
FIG. 15 is a flow chart of a method for controlling inductive power transmission from an exemplary external device to an IMD.

FIG. 15 is a flow chart 400 of a method for controlling power transmission from an external device 340 to IMD 310. At block 402, a power transmission signal is generated by the external device 340 under the control of power transfer control 350. The power transmission signal may be started manually, e.g., by a user interacting with user interface 346, automatically on a scheduled basis or in response to a sensor signal indicating a need for therapy, or automatically in response to detecting the IMD 310 within transmission range. IMD 310 may be detected as being in transmission range in response to a telemetry communication signal, e.g., confirmation of receipt of a telemetry wake-up signal or other techniques.

A signal is measured at block 404 for generating a power transmission feedback signal. In one embodiment, therapy delivery occurs when power transmission is occurring. In this embodiment, after starting the power transmission, the IMD power monitoring and regulator module 316 provides a rectified DC output signal to signal generator 322 for generating and delivering therapy. In other words, the power required by signal generator for generating and delivering a therapeutic signal is provided by power monitoring and regulator module 316 during inductive power transmission and when power transmission stops or is insufficient to power signal generator 322, therapy is not delivered.

In this embodiment, a feedback signal may be a measured amplitude of the delivered therapy pulses. Accordingly, the output pulse amplitude of therapy pulses generated by signal generator 322 may be measured and this amplitude may be transmitted as a feedback signal to the external device 340 at block 406. The feedback signal is used by power transfer control 350 at block 408 to adjust the transmitted power signal up or down as needed to regulate the output therapy pulse amplitude to a desired amplitude or within a range of a desired output amplitude. In some embodiments, the desired amplitude range is established based on other sensor feedback, e.g. an EMG signal. In this way, the control of output pulse amplitude is achieved through power transmission regulation using a closed-loop feedback signal. Variations in external device position, power status of external device 340 or other factors that may influence inductive coupling between external coil 352 and implanted coil 315 and variation in net power transmission to IMD 310 may be mitigated by adjusting the power transmission signal to maintain the pulse amplitude output at a desired level.

The feedback signal may additionally be used to generate a user display at block 410 to provide feedback to a user to notify the user that a therapy is in progress. The feedback signal display may be used to notify the user than an adjustment of body position and/or external device position is required to optimize power transmission.

In an alternative embodiment, an amplitude of the signal received by implanted coil 315 or the amplitude of a rectified Vout signal provided by monitoring and regulator module 316 may be measured at block 404 for generating a feedback signal transmitted to the external device at block 406. The power transfer control module 350 may adjust the power transmission signal to achieve a targeted received power by the IMD 310. In some cases, the power transmission signal may be reduced and still maintain a desired level of power transmission, thereby conserving the external power supply 364.

The feedback control signal may be provided on a continuously sampled basis or may be provided at regular intervals during a power transmission. In some embodiments, the feedback control signal may be requested by external device 340 via telemetry 354 when a change in patient activity, patient posture, EMG signal or other sensor signal is detected from external device sensors 358, IMD sensors 324, and/or remote sensors 302.

Power transmission feedback signal data may be stored in memory 344 for transmission to remote database/programmer/expert services 380. In some embodiments, the feedback signal may be transmitted to remote database/programmer expert services 380 in real or delayed time to enable an expert to assess the power transmission and therapy delivery functions for patient monitoring or troubleshooting purposes.

Figure 16:
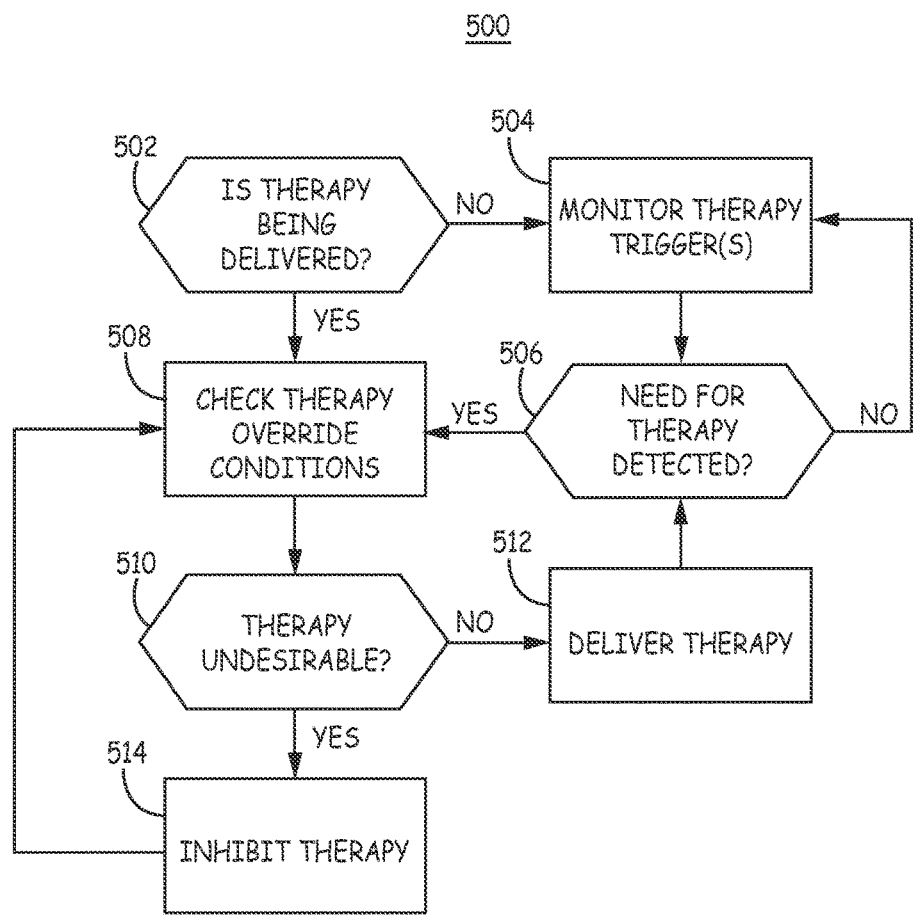
FIG. 16 is a flow chart of a method for controlling a therapy delivered by an exemplary implanted device.

FIG. 16 is a flow chart of a method 500 for controlling a therapy delivered by IMD 310 according to one embodiment. At block 502, if a stimulation therapy is not currently being delivered, therapy trigger signals are monitored at block 504. A therapy trigger signal may be a manual trigger entered by a user using external interface 346 or transmitted from remote database/programmer/expert services 380. A therapy trigger may be an automatic trigger generated in response to analysis of a sensor signal from IMD sensor(s) 324, external device sensor(s) 358 and/or remote sensors(s) 302. A sensor signal may indicate a need for therapy, e.g. an event detected by analysis of a sensor signal that meets a therapy delivery criterion, such as bladder activity or pressure. A sensor signal may alternatively indicate appropriate conditions for therapy delivery, such as a patient activity and/or posture condition that is/are desired for therapy delivery episodes.

A therapy trigger may additionally or alternatively be an automatic trigger provided by external device 340 or IMD controller 312 on a scheduled basis and/or upon external device 340 and IMD 310 coming into communication and power transmission range. Accordingly, multiple therapy trigger signals may be monitored for initiating a therapy and criteria for starting therapy may require one therapy trigger condition to be met or multiple trigger conditions to be detected in combination.

If a need for therapy is detected based on detecting a therapy trigger, as determined at block 506, the system 300 may evaluate one or more sensor signals or other device related conditions to determine if a therapy override condition is detected at block 508. If a therapy is undesirable, as determined at block 510, the therapy delivery is inhibited at block 514. If no therapy override condition is detected, therapy is delivered at block 512 by the IMD.

Therapy is delivered until a therapy episode of a predetermined time duration has expired or until a need for therapy is no longer detected at block 506. The therapy override conditions may be monitored throughout therapy delivery, and the therapy may be inhibited during therapy delivery if an undesirable therapy delivery condition is detected. Similarly, if therapy is inhibited at block 514, prior to starting or during therapy delivery, and a therapy override condition changes, as determined at blocks 508 and 510, therapy may be started or restarted if a therapy trigger is still being detected or a therapy session has not expired.

Therapy override conditions monitored at block 508 for detecting undesirable therapy delivery conditions at block 510 may include a patient activity state, patient posture, an EMG or nerve signal indicating intrinsic motor activity or other sensor-based condition, power transmission status, a power supply status or other conditions that would make therapy delivery undesirable for the sake of patient safety, patient convenience, therapy effectiveness or otherwise. The override condition may be detected from IMD sensors 324, remote sensor 302 and/or external device sensors 358. In some embodiments, the override condition may be manually entered by a user. The external device 340 and IMD 310 are therefore configured to cooperatively detect an activity state in response to an activity sensor signal and inhibit the therapeutic electrical stimulation by withholding the drive signal applied to the external coil 352 in response to a detected activity state corresponding to a previously defined therapy override condition.

Thus, various embodiments of a minimally invasive IMD system have been presented in the foregoing description with reference to specific embodiments. The various features and aspects of the IMD system described herein may be implemented in any combination other than the particular combinations shown in the illustrative embodiments, which may include adding or omitting some features. It is appreciated that various modifications to the referenced embodiments may be made without departing from the scope of the disclosure as set forth in the following claims.

The invention claimed is:

1. A system, comprising:
    an external medical device comprising:
        a control module for
            generating a drive signal having a signal pattern that indicates stimulation control parameters; and
            adjusting, in response to a feedback control signal, the signal pattern to indicate changes to the stimulation control parameters;
        an electrically conductive external coil coupled to the control module for receiving the drive signal; and
        an external telemetry module; and
    an implantable medical device comprising:
        an electrically conductive implantable coil for inductively coupling to the external coil and receiving an inductively coupled signal in response to the drive signal being applied to the external coil;
        a regulator module coupled to the implantable coil and configured to:
            produce, from the inductively coupled signal, a rectified voltage that varies according to an amount of power transferred by the inductively coupled signal,
            power the implantable medical device using the rectified voltage, and
            generate the feedback control signal correlated to an amplitude of the inductively coupled signal;
        a signal generator coupled to the regulator module to receive the rectified voltage and to generate a therapeutic electrical stimulation signal having a stimulation voltage that is set based upon the rectified voltage;
        a plurality of electrodes coupled to the signal generator for delivering the therapeutic electrical stimulation signal to a targeted therapy site; and
        an implantable telemetry module for transmitting the feedback control signal to the external telemetry module.

2. The system of claim 1, wherein the external coil comprises a plurality of external coils, the control module being configured to select, in response to the feedback control signal, an external coil from the plurality of external coils for inductive coupling to the implantable coil.

3. The system of claim 2, wherein the plurality of external coils comprises one of a plurality of coaxial coils and an array of coils.

4. The system of claim 2, wherein the plurality of external coils comprises a first coil having a first diameter and a second coil having a second diameter smaller than the first coil.

5. The system of claim 2, wherein the control module is configured to couple the drive signal to selected ones of the plurality of external coils in a plurality of combinations comprising at least one coil in each of the plurality of combinations and use the feedback control signal to select at least one of the plurality of coils for inductive coupling to the implantable coil.

6. The system of claim 1, wherein the external device further comprises a display for displaying to a user an indication of the feedback control signal.

7. The system of claim 1, wherein the regulator module is configured to generate the feedback control signal based upon an amplitude of the rectified voltage.

8. The system of claim 1, wherein the regulator module is configured to monitor the therapeutic electrical stimulation signal and generate the feedback control signal correlated to an amplitude of the therapeutic electrical stimulation signal, the control module configured to adjust the pattern of the drive signal to control the rectified voltage and the amplitude of the therapeutic electrical stimulation signal.

9. The system of claim 1, further comprising a physiological sensor for sensing a response to the therapeutic electrical stimulation signal,
    the regulator module configured to receive a physiologic sensor signal from the physiological sensor for generating the feedback control signal in response to the physiological sensor signal.

10. The system of claim 1, wherein
    the signal generator is configured to deliver the rectified voltage as the therapeutic electrical stimulation signal to the plurality of electrodes by operating as a switch between the plurality of electrodes and the rectified voltage.

11. The system of claim 10, wherein the control module is configured to adjust the pulse rate of the therapeutic electrical stimulation signal by adjusting the signal pattern of the drive signal to provide bursts of power at the pulse rate.

12. The system of claim 1, further comprising an activity sensor,
    the external device and the implantable device configured to cooperatively detect an activity state in response to an activity sensor signal and inhibit the therapeutic electrical stimulation signal by withholding the drive signal in response to a detected activity state.

13. The system of claim 12, wherein the external device being adapted to position the external coil for inducing an electromagnetic field along a tibial nerve region,
the implantable medical device being configured to deliver the therapeutic electrical stimulation signal to a tibial nerve,
the activity state corresponding to an intrinsic activation of the tibial nerve.

14. A method, comprising:
generating, by a control module of an external medical device, a drive signal applied to an electrically conductive external coil, the drive signal having a signal pattern that indicates stimulation control parameters, and
adjusting, by the control module, the signal pattern in response to a feedback control signal to indicate changes to the stimulation control parameters;
receiving, by an electrically conductive implantable coil of an implantable medical device, an inductively coupled signal when the drive signal is applied to the external coil;
producing, by a regulator module of the implantable medical device, a rectified voltage from the inductively coupled signal, the rectified voltage varying according to an amount of power transferred by the inductively coupled signal,
powering the implantable medical device using the rectified voltage;
generating, by the regulator module, the feedback control signal correlated to an amplitude of the inductively coupled signal;
transmitting, by a telemetry module of the implantable medical device, the feedback control signal to the external medical device;
receiving, at a signal generator of the implantable medical device, the rectified voltage,
generating, by the signal generator, a therapeutic electrical stimulation signal having a stimulation voltage that is set based upon the rectified voltage;
delivering the therapeutic electrical stimulation signal to a targeted therapy site using a plurality of electrodes coupled to the signal generator.

15. The method of claim 14, further comprising selecting an external coil from a plurality of external coils for inductive coupling to the implantable coil in response to the feedback control signal.

16. The method of claim 15, wherein selecting an external coil comprises selecting a coil from one of a plurality of coaxial coils or an array of coils.

17. The method of claim 15, wherein selecting an external coil comprises selecting one of a first coil having a first diameter and a second coil having a second diameter smaller than the first coil.

18. The method of claim 15, further comprising:
coupling the drive signal to selected ones of the plurality of external coils in a plurality of combinations comprising at least one coil in each of the plurality of combinations;
monitoring feedback signals associated with each of the plurality of combinations; and
selecting at least one of the plurality of coils in response to the feedback signals for inductive coupling to the implantable coil.

19. The method of claim 14, further comprising displaying an indication of the feedback control signal on a display.

20. The method of claim 14, further comprising:
generating the feedback control signal based on an amplitude of the rectified voltage.

21. The method of claim 14, further comprising:
monitoring the therapeutic electrical stimulation signal;
generating the feedback control signal correlated to an amplitude of the therapeutic electrical stimulation signal; and
adjusting the pattern of the drive signal to control the rectified voltage and the amplitude of the therapeutic electrical stimulation signal.

22. The method of claim 14, further comprising:
sensing a response to the therapeutic electrical stimulation signal using a physiological sensor;
receiving, at the regulator module a physiological sensor signal from the physiological sensor, and
generating, by the regulator module, the feedback control signal in response to the physiological sensor signal.

23. The method of claim 14, further comprising:
generating the drive signal having an amplitude, a pulse rate, and a pulse width;
rectifying the inductively coupled signal to generate the therapeutic electrical stimulation signal; and
delivering the therapeutic electrical stimulation signal to the plurality of electrodes by operating as a switch between the plurality of electrodes and the rectified voltage.

24. The method of claim 23, further comprising adjusting, the pulse rate of the therapeutic electrical stimulation signal by adjusting the signal pattern of the drive signal to provide bursts of power at the pulse rate.

25. The method of claim 14, further comprising:
detecting an activity state in response to an activity sensor signal; and
inhibiting the therapeutic electrical stimulation signal by withholding the drive signal in response to a detected activity state.

26. The method of claim 25, further comprising:
enabling an external device comprising the external coil to induce an electromagnetic field along a tibial nerve region of a patient when the drive signal is applied to the external coil;
delivering the therapeutic electrical stimulation signal to a tibial nerve; and
detecting the activity state corresponding to an intrinsic activation of the tibial nerve.

27. A medical device system, comprising:
an external primary coil;
a controller configured to apply a drive signal to the primary coil in a signal pattern that indicates stimulation control parameters, and configured to adjust the signal pattern to indicated changes to the stimulation control parameters in response to a feedback control signal;
an implantable secondary coil receiving an inductively coupled signal in response to the drive signal being applied to the primary coil;
a regulator module coupled to the secondary coil and configured to
produce, from the inductively coupled signal, a rectified voltage that varies according to an amount of power transferred by the inductively coupled signal,
power the implantable medical device using the rectified voltage, and
generate the feedback control signal correlated to an amplitude of the inductively coupled signal;

a signal generator coupled to the regulator module to receive the rectified voltage and to generate a therapeutic electrical stimulation signal having a stimulation voltage that is set based upon the rectified voltage.

\* \* \* \* \*